United States Patent [19]

Chang

[11] 4,161,489
[45] Jul. 17, 1979

[54] CONVERSION OF MIXTURES OF CARBON OXIDES AND HYDROGEN

[75] Inventor: Clarence D. Chang, Princeton, N.J.

[73] Assignee: Mobil Oil Corporation, New York, N.Y.

[21] Appl. No.: 806,797

[22] Filed: Jun. 15, 1977

[51] Int. Cl.$^2$ ............................................. C07C 1/04
[52] U.S. Cl. ...................... 260/449 R; 260/449.6 M; 260/449.6 R; 252/431 C; 252/474
[58] Field of Search ....... 260/449 R, 449 M, 449.6 R, 260/449.6 M

[56] References Cited

U.S. PATENT DOCUMENTS 3,979,332  9/1976  Kiovsky et al. ................. 260/449 M

OTHER PUBLICATIONS

393258, Beck et al., Alien Property Custodian, 1943.

Primary Examiner—Howard T. Mars
Attorney, Agent, or Firm—Charles A. Huggett; Carl D. Farnsworth

[57] ABSTRACT

Mixtures of hydrogen with oxides of carbon, preferably with carbon monoxide, are converted to hydrocarbons at temperatures below about 500° C. by contact with a fused alkali metal formate or hydroxide or mixtures thereof which contains a hydrogenation catalyst of a transition metal or a compound of a transition metal or mixture of the same.

5 Claims, No Drawings

CONVERSION OF MIXTURES OF CARBON OXIDES AND HYDROGEN

BACKGROUND OF THE INVENTION

1. Field of the Invention

This invention is concerned with a process for converting synthesis gas, i.e., mixtures of gaseous carbon oxides with hydrogen or hydrogen donors, to hydrocarbon mixtures and oxygenates. In one aspect, this invention is concerned with a process to convert such synthesis gas to hydrocarbon mixtures under conditions permitting good temperature control of the known exothermic reduction of carbon monoxide with hydrogen. In still another aspect, this invention is concerned with providing a novel catalyst system for conversion of synthesis gas to valuable hydrocarbon products rich in the valuable lower olefins ethylene and propylene.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353–433, (1966), Interscience Publishers, New York, New York, the contents of which are herein incorporated by reference. The techniques for gasification of coal or other solid, liquid, or gaseous fuel are not considered to be a part of this invention.

It is considered desirable to effectively and more efficiently convert synthesis gas, and thereby coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, at temperatures in the range of from about 300° F. to about 850° F. under pressures in the range of from about one to one thousand atmospheres pressure, over a fairly wide variety of catalysts. The Fischer-Tropsch process, for example, which has been most extensively studied, produces a range of products including liquid hydrocarbons, a portion of which have been used as low octane gasoline. The types of catalysts that have been studied for this and related processes included those based on metals or oxides of iron, cobalt, nickel, ruthenium, thorium, rhodium, and osmium.

The wide range of catalysts and catalysts modifications disclosed in the art and an equally wide range of conversion conditions for the reduction of carbon monoxide by hydrogen provide considerable flexibility toward obtaining selected boiling-range products. A review of the status of this art is given in "Carbon Monoxide-Hydrogen Reactions", Encyclopedia of Chemical Technology, Edited by Kirk-Othmer, Second Edition, Volume 4, pp. 446–488, Interscience Publishers, New York, New York, the text of which is incorporated herein by this reference. See also H. H. Storch, N. Golumbic & R. B. Anderson "The Fischer-Tropsch and Related Synthesis", John Wiley & Sons, Inc., New York, New York.

The hydrogenation of carbon oxides is highly exothermic and the various processes which involve this reaction must include means to remove the heat of reaction. These processes include Fischer-Tropsch synthesis, the Oxo process, methanation, methanol synthesis, and the like. It has been proposed to use liquid systems to aid in heat exchange. For example, that technique is utilized by the heavy slurry oil process and by the fused salt medium described in German Offenlegungsschrift No. 2603-892. According to the disclosure in the latter citation synthesis gas mixtures of hydrogen with oxides of carbon are reacted at temperatures above 500° C. in a bath of molten alkali metal halides or carbonates in which is dispersed finely divided metal, metal oxides or carbides to produce methane.

SUMMARY OF THE INVENTION

It has now been demonstrated that synthesis gas is converted to hydrocarbon mixtures by contact with a transition metal or metal oxide dispersed or dissolved in a molten bath of alkali metal hydroxide or formate which may contain carbonate at temperatures below 500° C., preferably 150°–350° C. It is known that carbon monoxide will react with caustic to produce the formate of the alkali metal, hence supply of a carbon monoxide-hydrogen mixture to a bath of molten alkali metal hydroxide probably produces formates in situ. Without intending to be bound to any theory, it is postulated that alkali formate may be an intermediate in the conversion to hydrocarbons by the present process. Whatever may be the explanation of the results obtained, it has been demonstrated that formates and hydroxides are unique among the materials so far tested for the purpose. Some metal chlorides and alkali metal thiocyanates have been found ineffective as liquid media for the same purpose.

DESCRIPTION OF SPECIFIC EMBODIMENTS

In general, the reaction of this invention will be carried out at elevated temperatures from melting point of the fused salt (or caustic) bath up to 500° C. and above. Low temperature baths may be obtained by suitable eutectic mixtures, but in any event, temperatures of at least 100° C., preferably above 150° C. are employed. Pressure does not appear to be a critical parameter, but elevated pressures are favored to obtain reasonable throughput, generally in the range of 500 to 1000 psig. At lower pressures, as low as atmospheric and below, the reaction proceeds but usually at less than preferred rates of throughput. Higher pressures than 1000 psig can be employed, say up to 7500 psig, but at increased cost for capital investment and operating expenses for high pressure vessels, compressors and the like.

Appropriately, the charge of hydrogen and oxides of carbon is introduced to the bottom of the molten salt or caustic bath by spargers for conversion on passing upwardly through the catalyst bath. Space velocity may vary from 0.01 unit weight of charge per unit of catalyst bath per hour, up to 10 WHSV or higher.

The charge will usually contain an excess of hydrogen above the stoichiometric equivalent, preferably around four moles of hydrogen per mole of carbon oxide, preferably carbon monoxide. That ratio of reactants may be varied within fairly wide limits as recognized in the art for synthesis gas supplied in other types of reactors.

As noted, the catalyst is a solution or suspension of transition metal or transition metal compound, such as the oxide, in a liquid medium of fused alkali metal formate or hydroxide. The hydrogenation metal (or compound) may be any of those metals classified as transition metals, including the metals of Group II B of the Periodic Table. Particularly preferred are the metals of Group VIII of the Periodic Table. The metal or metal compound, when used in the form of a solid dispersed in the fused bath, will be supplied in finely divided form to provide maximum surface area available for catalysis of the reaction between hydrogen and oxides of carbon. At the temperatures employed, water formed in the reaction is in vapor form and leaves the reactor with the reaction products and unreacted charge material. The fused bath is circulated in part through suitable heat exchangers for temperature control.

EXAMPLE 1

A 300 ml. stirred autoclave was charged with 23.53 g. sodium formate, 29.10 g. potassium formate and 0.6 g. rhodium chloride ($RhCl_3 \cdot 3 H_2O$). The vessel was evacuated and a mixture of hydrogen and carbon monoxide in the ratio of 4 moles hydrogen per mole of carbon monoxide was admitted until a pressure of 1 atmosphere was reached. The autoclave was then heated to 200° C. and the stirrer started. Additional charge mixture of 4/1 hydrogen, carbon monoxide was added to a total pressure of 1000 psig. After 3 hours, 15 minutes of reaction, the vapor content of the autoclave was drawn off through a trap cooled by liquid nitrogen. The product showed presence of hydrocarbons by vapor phase chromatography, together with carbon dioxide and possibility of some dimethyl ether. Product inspection is reported in Table 1.

EXAMPLES 2 & 3

Runs essentially similar to Example 1 were conducted at 500 and 1000 psig with the same formate salt bath and replacement of the rhodium catalyst by iron oxide catalyst prepared for ammonia synthesis. The results are shown in Table 1 together with data on fluidized bed Synthol process and heavy oil slurry process taken from the technical literature.

It is particularly noteworthy that the present process yields relatively large amounts of the valuable lower olefins ethylene and propylene.

TABLE 1

SYNGAS CONVERSION IN FUSED FORMATE

| | Fused Salt | | | Fluid Bed Synthol (a) | Hvy Oil Slurry 2.6% Fe (b) |
|---|---|---|---|---|---|
| Example | 1 | 2 | 3 | | |
| Catalyst | 1% $RhCl_3$ | 5% $Fe_3O_4$ | | | |
| T° C. | 250 | 200 | 200 | 220–240 | 273 |
| P, psig | 1000 | 500 | 1000 | 300 | 140 |
| $H_2/CO$ | 4 | 4 | 4 | 3 | 2 |
| Conversion, % | | | | | |
| CO | 1 | 78 | 79 | High | 78.5 |
| $H_2$ | 1 | 69 | 43 | High | — |
| Products, wt. % | | | | | |
| $C_1$ | — | 13.6 | 21.4 | 13.1 | 2.2 |
| $C_2$ | 27.5 | 10.6 | 12.9 | 5.8 | — |
| $C_3$ | 46.1 | 9.6 | 9.0 | 3.4 | — |
| $C_4$ | 7.6 | 6.7 | 3.9 | 3.2 | 0.6 |
| $C_5$–$C_{11}$ | — | 2.8 | 4.8 | 10.0 | 0.9 |
| $C_{12}$–$C_{20+}$ | — | — | — | 2.0 | 30.1 |
| Total Paraffins | 81.2 | 43.3 | 52.0 | 37.5 | 33.8 |
| $C_2^=$ | 2.1 | 14.2 | 13.6 | 4.4 | 2.6 |
| $C_3^=$ | 1.3 | 23.9 | 18.7 | 12.8 | |
| $C_4^=$ | — | 14.0 | 6.8 | 10.0 | |
| $C_5^=$–$C_{11}^=$ | — | 4.0 | 8.1 | 23.4 | 3.4 |
| $C_{11}^=$–$C_{20}^=$ | — | — | — | 3.1 | 49.9 |
| Total olefins | 3.4 | 56.1 | 47.2 | 53.7 | 60.4 |
| Aromatics | 3.3 | — | — | — | — |
| Oxygenates | 12.1 | 0.6 | 0.8 | 8.8 | 5.8 |

(a) Hydrocarbon Proc. (Nov. 1974), p. 143.
(b) Sekigu Gakkai Shi 17 (10), 863 (1974).

EXAMPLES 4–8

For purposes of comparison, data are provided in Table 2 on attempts to react synthesis gas of 4 moles of hydrogen per mole of carbon monoxide in fused salt baths of salts other than formates and containing transition metal catalyst. No hydrocarbons were found in the product, only traces of water and carbon dioxide.

TABLE 2

| Example No. Catalyst | Temp °F. | psig | WHSV | Products |
|---|---|---|---|---|
| Ex. 4 0.2% Pt in $SnCl_2$ | 485 | 600 | 0.016 0.16 0.002 | $H_2O$, $CO_2$ |
| Ex. 5 0.3% Pt in $ZnCl_2$ | 557 | 600 | 0.036 0.32 | Traces $H_2O$, $CO_2$ |
| Ex. 6 0.5% Pt in KSCN | 390 | 600 | 0.042 0.009 0.38 | Traces $H_2O$, $CO_2$, COS |
| Ex. 7 6% Co in $SnCl_2$ | 568 | 600 | 0.008 0.05 0.10 | Traces $H_2O$, $CO_2$ |

I claim:
1. A process for converting synthesis gas comprising hydrogen and carbon monoxide to hydrocarbons which comprises, passing synthesis gas through a molten bath comprising alkali metal formate in which molten bath a transition metal or a transition metal compound having activity for reducing carbon monoxide is dispersed and maintaining the temperature of said molten bath within the range of 150° C. to 350° C. and its pressure within the range of 500 to 1,000 psig.

2. A process according to claim 1 wherein said metal compound is iron oxide.

3. A process according to claim 1 wherein said metal compound is rhodium chloride.

4. A process according to claim 1 wherein said alkali metal is potassium.

5. A process according to claim 1 wherein said alkali metal is sodium.

* * * * *